(12) United States Patent
Chang et al.

(10) Patent No.: US 6,253,599 B1
(45) Date of Patent: Jul. 3, 2001

(54) PRESSURE VESSEL TESTING FIXTURE

(75) Inventors: Dick J. Chang, Los Angeles; Pierre R. Valenzuela, Pico Rivera, both of CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 09/325,113

(22) Filed: Jun. 3, 1999

(51) Int. Cl.[7] .............................. G01N 3/10; F16L 33/22
(52) U.S. Cl. ........................ 73/49.8; 73/49.1; 73/49.5; 285/323
(58) Field of Search ........................ 73/49.1, 49.5, 73/49.6, 837, 840, 49.8; 220/243, 315, 319, 320, 327, 328; 285/323, 911

(56) References Cited

U.S. PATENT DOCUMENTS

| | | | |
|---|---|---|---|
| 3,593,573 | * 7/1971 | Ely | 73/49.8 |
| 3,884,070 | * 5/1975 | Windle | 73/49.8 |
| 4,197,733 | * 4/1980 | Holland et al. | 73/49.1 |
| 4,646,561 | * 3/1987 | Toelke | 73/49.5 |
| 4,799,717 | * 1/1989 | Kingsford | 285/341 |
| 5,217,261 | * 6/1993 | DeWitt et al. | 285/333.2 |
| 5,222,772 | * 6/1993 | McGraw | 285/323 |
| 5,511,830 | * 4/1996 | Olson et al. | 285/243 |
| 5,638,869 | 6/1997 | Zaborszki et al. . | |

FOREIGN PATENT DOCUMENTS

| | | | |
|---|---|---|---|
| 2197410 | * 5/1988 | (GB) | 285/323 |
| 02261995 | * 10/1990 | (JP) | 285/323 |

* cited by examiner

Primary Examiner—Hezron Williams
Assistant Examiner—Michael Cygan
(74) Attorney, Agent, or Firm—Derrick Michael Reid

(57) ABSTRACT

Opposing end fittings of a cylindrical tube pressure test fixture uses slanted abutting surfaces between retaining rings and ferrules that securely clamps a tube under high pressure testing. Retaining ring and ferrule friction and applied radial compression induce shear force upon the tube and prevent leaks during pressure testing.

8 Claims, 1 Drawing Sheet

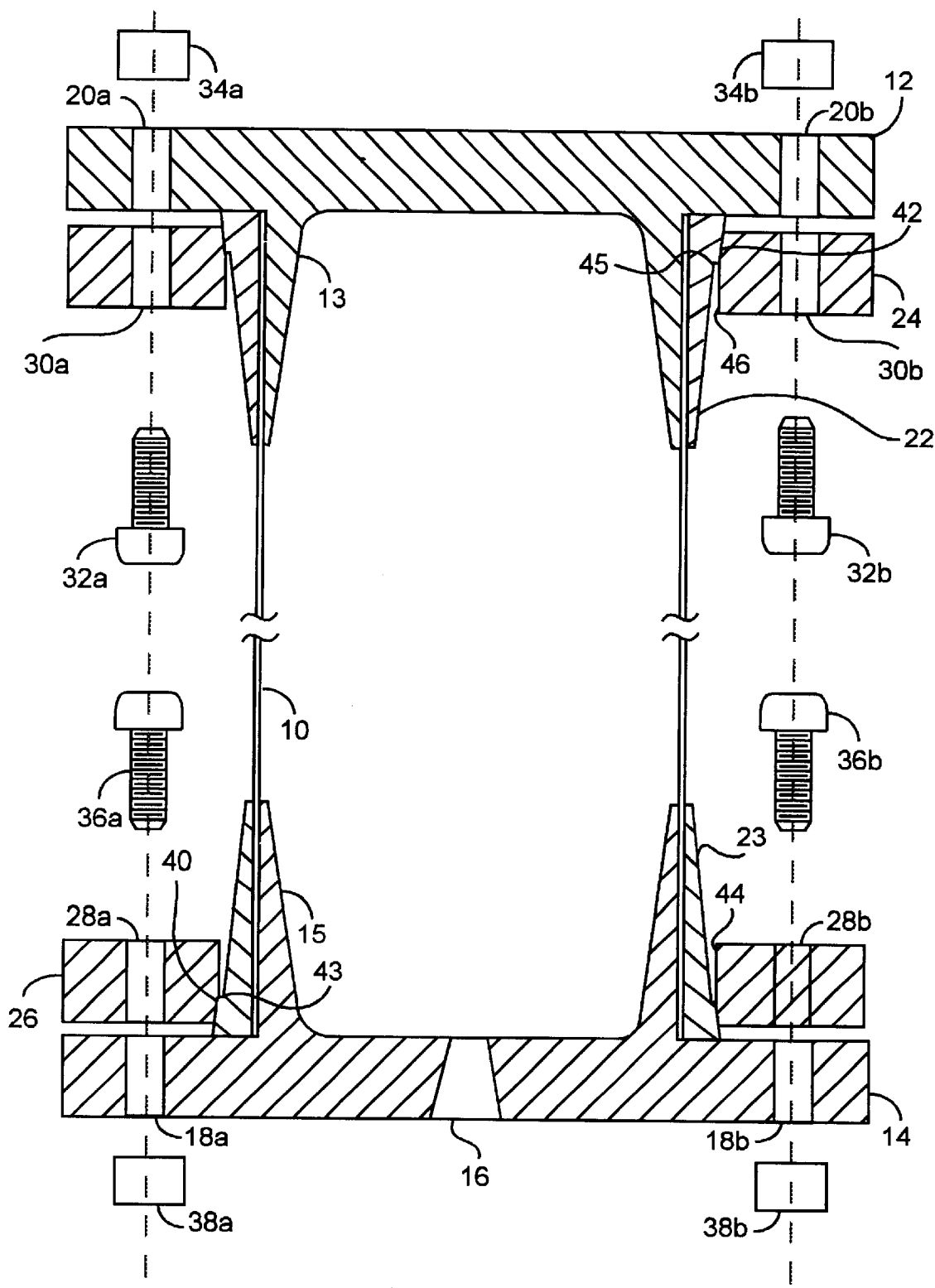

PRESSURE VESSEL TESTING FIXTURE

STATEMENT OF GOVERNMENT INTEREST

The invention was made with Government support under contract No. F04701-93-C-0094 by the Department of the Air Force. The Government has certain rights in the invention.

FILED OF THE INVENTION

The invention relates to the field of pressure testing pressure vessels. More particularly, the present invention relates to pressure testing cylindrical tubes.

BACKGROUND OF THE INVENTION

Composite pressure vessels are often fabricated as cylindrical tubes with hemispherical end caps. During the fabrication process, the filaments of graphite or glass are wound in a continuous pattern including both the cylindrical portion and the end caps. For materials and structures testing purposes, a cylindrical tube is an ideal specimen to represent the cylindrical portion of the vessel. For example, a composite cylindrical tube can be fabricated by either filament winding or tape wrapping techniques to have the same lay-ups angle as a cylindrical portion of a pressure vessel. The cylindrical tubes so fabricated will have the same mechanical properties as the cylindrical portion of the pressure vessel. The tube, however, can be fabricated at a small fraction of the cost of a pressure vessel with integral end caps.

A problem associated with realistic pressure testing of cylindrical specimens is that the tube ends must be sealed in such a manner that the tube does not leak, that there are no induced bending stresses at the interface between the tube and the end cap, and that the axial load of the internal pressure is carried by the cylindrical walls of the tube. In typical designs, a metal flange with an insert is utilized to bond the tube specimen using adhesive. The adhesive is under shear stress when the tube is internally pressurized. The shear strength of the adhesive depends upon the type of adhesive used, the bonding procedure, the material for the adherent, and the cure operation. However, regardless of how careful the bonding operation is conducted, the failure of a cylindrical composite tube under internal pressure often occurs at the end fitting of the tube interface. These and other disadvantages are solved or reduced using the invention.

SUMMARY OF THE INVENTION

An object of the invention is to provide a test fixture for pressure testing cylindrical tubes.

Another object of the invention is to provide end fitting fixtures for cylindrical composite tubes under high internal pressure.

Yet another object of the invention is to provide a test fixture for pressure testing cylindrical tubes to provide increased shear tension and to prevent leaks during pressure testing.

The present invention is directed to an improved end fitting test fixture for cylindrical composite tubes tested under high internal pressure. The ends of the tube are inserted into opposing end fixtures having a vertically extending flange abutting the inner walls of the tubes at both ends. A ferrule is disposed around and abuts the outer walls of the tube. A retaining ring is disposed around the ferrule, both of which have mating slanted abutting surfaces. The retaining ring is clamped down upon the end fixtures, the slanted abutting surfaces slide against each to apply a normal radial compression to the tube interface between the tube and flange at the inner walls of the tube, and between the tube and ferrule at the outer walls of the tube. This compression will generate a mechanical friction force, that is a shear force when the tube and the end fitting are being pulled apart longitudinally under high internal pressure testing. The radial compression increases the shear strength of the end fitting by an amount equal to the product of the compressive stress, the friction coefficient, and the contact area between the tube and the ferrule. The compression not only secures the tubes in the fixture but prevents leaks at the tube ends when inserted into the fixtures. These and other advantages will become more apparent from the following detailed description of the preferred embodiment.

BRIEF DESCRIPTION OF THE DRAWING

The drawing is a cross sectional view of the pressure test fixture with a cylindrical tube secured therein.

DETAILED DESCRIPTION OF THE PREFERRED EMBODIMENT

An embodiment of the invention is described with reference to the drawing using reference designations as shown in the drawing. The drawing is oriented top to bottom along the elongated vertical length of a cylindrical tube specimen 10. The drawing depicts the cross-sectional view of the test fixture. The test fixture provides the generation of shear strength between the tube 10 and opposing top and bottom, circular, end fittings caps 12 and 14, respectively through radial compression induced friction. Opposing top and bottom ends of the tube 10 are respectively disposed in the end caps 12 and 14 aligned by vertically extending, tubular shaped, tapered flanges 13 and 15, respectively, abutting the inner wall of respective bottom end portion of the tube 10, as shown. One of the caps, such as bottom end cap 14 has a gas pressure aperture 16 for pressurizing the tube 10 during pressure testing.

The bottom end cap 14 has a plurality of circumferentially disposed, vertically extending, clamping bolt holes 18*a* through 18*b* aligned with an equal number of a plurality of circumferentially disposed, vertically extending, clamping bolt holes 20*a* through 20*b* of the top end cap 12. The top cap 12 is aligned with the bottom cap 14 relative to bolt holes 18*ab* and 20*ab*. Top and bottom, vertically extending, tapered, ring shaped ferrules 22 and 23 are circumferentially disposed around and abutting the outer wall of respective top and bottom end portions of the tube 10. The ferrules 22 and 23 function to provide for radial compression between the outer wall of the ends of the tube 10 and the inner surface of the ferrules 22 and 23. Opposing, top and bottom retaining rings 24 and 26 are circumferentially disposed around respective ferrules 22 and 23 to create a radial compression force upon ferrules 22 and 23 that translates this radial compression force at the interface between the ferrules 22 and 23 and respective outer walls of the opposing ends of the tubes 10 retained by respective flanges 13 and 15. The bottom retaining ring 26 has an equal number of a plurality of circumferentially disposed, vertically extending bolt holes 28*a* through 28*b* aligned with respective holes 18*a* through 18*b* of the bottom end cap 14. The top retaining ring 24 has an equal number of a plurality of circumferentially disposed, vertically extending bolt holes 30*a* through 30*b* aligned with respective holes 20*a* through 20*b* of the top end cap 14. The end caps 12 and 14 are substantially circular plates having respective outer radially extending flanges though which the respective holes 18*ab* and 20*ab* extend. Hence, the radially extending flange of the caps 12 and 14 and the retainer rings 24 and 26 have a plurality, such as sixteen, bolt holes 18*ab*, 20*ab*, 28*ab*, and 30*ab* aligned at the same respectively radial and angular locations. The retainer rings 24 and 26 have an outer diameter equal to that of the radially extending flange having the holes 18*ab* and 20*ab* of the caps 12 and 14. An equal number of clamping bolts 32*a* through 32*b* are received by an equal number of clamping nuts 34*a* through 34*b* respective through bolt holes 20*a* through 20*b* of the top end cap 12 and through bolt holes 30*a* through 30*b* of the top retaining ring 24. An equal number of clamping bolts 36*a* through 36*b* are received by an equal number of clamping nuts 38*a* through 38*b* respective through bolt holes 18*a* through 18*b* of the bottom end cap 14 and through bolt holes 28*a* through 28*b* of the bottom retaining ring 26.

The retainer rings 24 and 26 and respective ferrules 22 and 23 function to induce compression with increased shear load capability significantly and to prevent leaks during pressure testing. The bottom retaining ring 26 and the bottom ferrule 23 have matching off axis, slanted surfaces forming a slanted abutting interface 40. The top retaining ring 24 and the top ferrule 22 have matching off axis, slanted surfaces forming a slanted abutting interface 42. The bottom tapered ferrule 23 has an outer radially extending lip 43 juxtaposed the interface 40, so that when the bottom tapered ferrule 23 is abutting the bottom retaining ring 26, a gap 44 is created between bottom ferrule 23 and the bottom retaining ring 26. The top tapered ferrule 22 has an outer radially extending lip 45 juxtaposed the interface 42, so that when the top tapered ferrule 22 is abutting the top retaining ring 24, a gap 46 is created between top ferrule 22 and the top retaining ring 24. The ferrules 22 and 23 have tapered thickness that is thicker near the end caps 12 and 14 and thinner away from the end caps 12 and 14. The thin portion of ferrules 22 and 23 at the tip away from the caps 12 and 14 provide for high radial compliance so that no high stress concentration develops between the ferrules 22 and 23 and the tube 10 that may induce premature failure. The retainer rings 24 and 26 have an inner diameter slightly smaller than the outside diameter of the ferrules 22 and 23 so as to interfere with each other to respectively create the interfaces 40 and 42.

To generate the normal compression and thus to increase the shear bonding strength between the inner walls of the ferrules 22 and 23 and the outer wall of the top and bottom ends of the tube 10, the bolts 32*ab* and 36*ab* are respectively screwed into respectively nuts 34*ab* and 38*ab*, so as to clamp the retaining rings 24 and 26 respectively towards the end caps 12 and 14, so as to respectively and radially force the retaining rings 24 and 26 against opposing ferrules 22 and 23 as the rings 24 and 26 slide in friction against ferrules 22 and 23, so as to apply a radial compression force against the ferrules 22 and 23 that in turn translated this compression force against the outer walls of the ends of the tube 10 to thereby securely fasten and clamp the tube 10 in the end caps 12 and 14 between the flanges 13 and 15 and the respective ferrules 22 and 23.

In assembling the test fixture, the inner walls of the ends of the tube 10 are first bonded to the outer walls of the flanges 13 and 15. The outer walls of the ends of the tube 10 is then bonded to the inner surface of the ferrules 22 and 23. The interface 40 and 42 between the retainer rings 24 and 26 and the respective ferrules 22 and 23 introduce the gaps 46 and 44, respectively, between the retainer rings 24 and 26 and the ferrules 22 and 23. The rings 24 and 26 are then forced by tightening the bolts 32*ab* and 36*ab* through the holes 20*ab* and 30*ab*, and 18*ab* and 28*ab*. This tightening forces the inner walls of ferrules 22 and 23 against the outer walls of the tube 10 and against the outer walls of flanges 13 and 15 in radial compression. This radial compression increases the shear strength between the tube 10 and both of the ferrules 22 and 23 and flanges 13 and 15 by an amount equal to NAX where X is the frictional coefficient, N is the normal compressive stress, and A the total contact area between the tube 10 and the ferrules 22 and 23 and between the tube 10 and the flanges 13 and 15.

In an exemplar test, tube specimens 10 of filament wound. graphite-epoxy thin wall tubes were tested. The tube 10 was made of Toho G30-500-3K graphite filaments in an epoxy resin. The tubes 10 had a nominal inner diameter of 4.0 inches with a nominal wall thickness of 0.060 inches. The lay-up angles of the tubes were $(10/-10/90)_3$. The length of the tube specimen 10 was 17.5 inches. The outer diameter of the flange and the retainer plate is 6.0 in. The inner diameter of the retainer ring varies from 4.26 to 4.361 in. The length of the inner insert and the ferrule is 1.5 inches. The thickness of the inner insert is tapered from 0.050 to 0.376 inches and the thickness of the ferrule varies from 0.094 to 0.188 inches. The resulting gaps 44 and 46 between the flange and the retainer plates are 0.050 inches. Based on the tensile strength of 550 ksi for the Toho graphite filaments and 60% fiber volume fraction, the burst pressure was about 4000 psi. The high pressure translates to a total load of 50300 lb or a linear load of 4000 lb per linear inch of circumference. More than three dozen tube specimens had failures away from the fitting interface at various internal pressure levels depending upon the degrees of induced damages to the tubes.

The present invention provides for generation of additional shear strength between a cylindrical tube specimen 10 and end fitting caps 12 and 14 through radial compression induced friction. The radial compression between the tube specimen 10 and adjacent end fitting ferrules 22 and 23 and inner flanges 13 and 15 is based on slanted interface 40 and 42 between the retainer rings 24 and 26 and the respective ferrules 22 and 23. The induced compression has increased the shear load capability significantly, thereby preventing leaks at the end caps 12 and 14, to properly test the tube pressure strength. Those skilled in the art can make enhancements, improvements and modifications to the invention, and these enhancements, improvements and modifications may nonetheless fall within the spirit and scope of the following claims.

What is claimed is:

1. A fixture for pressure testing a cylindrical tube, the fixture comprising, top and bottom end caps comprising respective circular vertically extending flanges having respective outer walls for receiving an inner wall of respective ends of the cylindrical tube, comprising respective circular radially extending outer flanges, and comprising an aperture for communicating a pressurized gas within the cylindrical tube, top and bottom ferrules comprising respective vertically extending inner walls for receiving an outer wall of the respective ends of the cylindrical tube, and comprising respective slanted outer surfaces, top and bottom retaining rings comprising respective slanted inner surfaces for respective abutment to the respective slanted outer surfaces of the top and bottom ferrules, the respective slanted inner surfaces and respective slanted outer surfaces abut to form respective slanted interfaces between the top and bottom retaining rings and the top and bottom ferrules, and tightening means for vertically clamping together respectively the respective circular radially extending outer flanges of the top and bottom end caps to the top and bottom retaining rings, the respective slanted inner surfaces slide against the respective slanted outer surfaces at the respective slanted interfaces to create respective radial compression forces between the respective vertically extending inner walls of the top and bottom ferrules and the outer wall of the cylindrical tube and between the inner wall of the cylindrical tube and the respective outer walls of the respective circular vertically extending flanges when tightening the tightening means to secure the cylindrical tube in the top and bottom end caps, to clamp rigidly the ends of cylindrical tube, the ends of the cylindrical tube transmitting the respective radial compressive forces to the respective circular vertically extending flanges for increasing frictional forces between the ends of the cylindrical tube and the respective ferrules and circular vertically extending flanges for increased pressurization during pressure testing.

2. The fixture of claim 1 wherein the tightening means comprises a plurality of bolt holes circumferentially disposed in radial angular alignment around both of the respective circular radially extending flanges of the top and bottom end caps and the top and bottom retaining rings, and comprises a plurality of pairs of bolts and respective nuts extending through the plurality of bolt holes.

3. The fixture of claim 2 wherein, a first set of the plurality of pairs of bolts and respective nuts are for clamping together the top end cap to the top retaining ring, and a second set of the plurality of pairs of bolts and respective nuts are for clamping together the bottom end cap to the bottom retaining ring.

4. The fixture of claim 1 further comprises an adhesive disposed between the respective outer walls of the respective circular vertically extending flanges and the inner wall of the cylindrical tube and between the respective inner walls of the top and bottom ferrules and the outer wall of the cylindrical tube.

5. The fixture of claim 1 wherein respective slanted outer surfaces of the top and bottom ferrules comprise respective radially extending lips for defining respective gaps between the respective slanted outer surfaces of the top and bottom ferrules and the top and bottom retaining rings.

6. A fixture for pressure testing a cylindrical tube, the fixture comprising, top and bottom end caps comprising respective circular vertically extending flanges having respective outer walls for receiving an inner wall of respective ends of the cylindrical tube, comprising respective circular radially extending outer flanges, comprising first respective sets of a plurality of bolt holes circumferentially disposed in radial angular alignment around the respective circular radially extending flanges, and comprising an aperture for communicating a pressurized gas within the cylindrical tube, top and bottom ferrules comprising respective vertically extending inner walls for receiving an outer wall of the respective ends of the cylindrical tube, and comprising respective slanted outer surfaces, top and bottom retaining rings comprising respective slanted inner surfaces for respective abutment to the respective slanted outer surfaces of the top and bottom ferrules, and comprising second respective sets of a plurality of bolt holes circumferentially disposed in radial angular alignment around the top and bottom retaining rings, the respective slanted inner surfaces and respective slanted outer surfaces abut to form respective slanted interfaces between the top and bottom retaining rings and the top and bottom ferrules, and first and second sets of a plurality of pairs of bolts and nuts respectively vertically extending in radial alignment through the first and second respective sets of the plurality of bolt holes for respectively vertically clamping together the respective circular radially extending outer flanges of the top and bottom end caps to the top and bottom retaining rings, the respective slanted inner surfaces slide against the respective slanted outer surfaces at the respective slanted interfaces to create respective radial compression forces between the respective vertically extending inner walls of the top and bottom ferrules and the outer wall of the cylindrical tube and between the inner wall of the cylindrical tube and the respective outer walls of the respective circular vertically extending flanges when respectively tightening together the first and second set of pairs of bolts and nuts to secure the cylindrical tube in the top and bottom end caps, to clamp rigidly the ends of cylindrical tube, the ends of the cylindrical tube transmitting the respective radial compressive forces to the respective circular vertically extending flanges for increasing frictional forces between the ends of the cylindrical tube and the respective ferrules and circular vertically extending flanges for increased pressurization during pressure testing.

7. The fixture of claim 6 further comprises an adhesive disposed between the respective outer walls of the respective circular vertically extending flanges and the inner wall of the cylindrical tube and between the respective inner walls of the top and bottom ferrules and the outer wall of the cylindrical tube.

8. The fixture of claim 6 wherein respective slanted outer surfaces of the top and bottom ferrules comprise respective radially extending lips for defining respective gaps between the respective slanted outer surfaces of the top and bottom ferrules and the top and bottom retaining rings.

* * * * *